United States Patent
Schuman et al.

(10) Patent No.: US 6,440,072 B1
(45) Date of Patent: Aug. 27, 2002

(54) MEDICAL DIAGNOSTIC ULTRASOUND IMAGING SYSTEM AND METHOD FOR TRANSFERRING ULTRASOUND EXAMINATION DATA TO A PORTABLE COMPUTING DEVICE

(75) Inventors: Aaron J. Schuman, Mountain View; Sankaralingam R. Ramraj, Cupertino; Aline A. Baeck; Janice L. Marshall, both of Sunnyvale; Douglas Gallinat, San Jose, all of CA (US)

(73) Assignee: Acuson Corporation, Mountain View, CA (US)

( * ) Notice: Subject to any disclaimer, the term of this patent is extended or adjusted under 35 U.S.C. 154(b) by 0 days.

(21) Appl. No.: 09/538,320

(22) Filed: Mar. 30, 2000

(51) Int. Cl.⁷ .................................................. A61B 8/00
(52) U.S. Cl. ..................................................... 600/437
(58) Field of Search ................................. 600/437, 443, 600/447, 444–446, 549; 128/903, 916; 364/708.1; 382/128

(56) References Cited

U.S. PATENT DOCUMENTS

| | | |
|---|---|---|
| 3,972,320 A | 8/1976 | Kalman |
| 4,100,916 A | 7/1978 | King |
| 4,413,629 A | 11/1983 | Durley, III |
| 4,522,213 A | 6/1985 | Wallroth et al. |
| 4,974,607 A | 12/1990 | Miwa |
| 5,291,399 A | 3/1994 | Chaco |
| 5,603,323 A | 2/1997 | Pflugrath et al. |
| 5,640,960 A | 6/1997 | Jones et al. |
| 5,715,823 A | 2/1998 | Wood et al. |
| 5,778,177 A | 7/1998 | Azar |
| 5,851,186 A | 12/1998 | Wood et al. |
| 5,867,821 A | 2/1999 | Ballantyne et al. |
| 5,891,035 A | 4/1999 | Wood et al. |
| 5,944,659 A | 8/1999 | Flach et al. |
| 5,957,846 A * | 9/1999 | Chiang et al. ............... 600/447 |
| 5,964,709 A * | 10/1999 | Chiang et al. ............... 600/447 |
| 6,106,472 A * | 8/2000 | Chiang et al. ............... 600/447 |
| 6,248,073 B1 * | 6/2001 | Gilbert et al. ............... 600/447 |
| 6,349,143 B1 * | 2/2002 | Hastings et al. ............ 382/128 |
| 2001/0044588 A1 * | 3/2001 | Mault et al. ................ 600/549 |

* cited by examiner

*Primary Examiner*—Marvin M. Lateef
*Assistant Examiner*—Ali M. Imam (57) ABSTRACT

The preferred embodiments described herein provide a medical diagnostic ultrasound imaging system and method for transferring ultrasound examination data to a portable computing device. In one preferred embodiment, ultrasound examination data is transferred from a medical diagnostic ultrasound imaging system to a portable computing device, such as a personal digital assistant. The ultrasound examination data can be viewed on the portable computing device or further transferred to a review station or another portable computing device for review. In some preferred embodiments, the examination data is converted from a form readable by the ultrasound system to a form readable by the portable computing device or review station. The ultrasound examination data can be transferred using a wired connection or using wireless technology, such an infrared communications link. The preferred embodiments can also be used with other medical acquisition devices and medical examination data. Examination data can also be transferred from medical networks, such as a medical diagnostic ultrasound imaging network.

35 Claims, 4 Drawing Sheets

MEDICAL DIAGNOSTIC ULTRASOUND IMAGING SYSTEM AND METHOD FOR TRANSFERRING ULTRASOUND EXAMINATION DATA TO A PORTABLE COMPUTING DEVICE

BACKGROUND

In many medical applications, it is often desired to view a medical image on a device other than the acquisition device that generated the image. For example, in some environments, an ultrasound imaging system is hard-wired to an image network, and computer review stations at remote locations can access and view images generated by the ultrasound system. In non-network environments and in other applications, images are transferred to viewing devices using "sneakernet" transfer: images generated by the ultrasound system are stored on portable storage media (such as a videotape or a magneto-optical ("MO") disk), and the portable storage media is physically carried from the ultrasound system to a viewing device (such as a television with a VCR or a computer review station).

There are several disadvantages associated with the sneakernet approach. First, this approach often makes inefficient use of the relatively large storage capacity of the portable storage media. For example, in many situations, an entire videotape is used to transfer a few seconds or minutes of image data. Further, videotapes are bulky and susceptible to stretching, overheating, and decay. Additionally, difficulties arise when the ultrasound system and the viewing device do not support the same type of portable storage media. For example, although many ultrasound systems use videotape to store images, computer review stations typically do not have a VCR to play the stored images. Also, this approach requires the user to be familiar with the operation of the ultrasound system (to transfer an image from the system to the portable storage media) as well as the operation of the viewing device (to transfer the image from the portable storage media to the viewing station).

There is a need, therefore, for a medical diagnostic ultrasound imaging system and method that overcomes the disadvantages described above.

SUMMARY

The present invention is defined by the following claims, and nothing in this section should be taken as a limitation on those claims.

By way of introduction, the preferred embodiments described below provide a medical diagnostic ultrasound imaging system and method for transferring ultrasound examination data to a portable computing device. In one preferred embodiment, ultrasound examination data is transferred from a medical diagnostic ultrasound imaging system to a portable computing device, such as a personal digital assistant. The ultrasound examination data can be viewed on the portable computing device or further transferred to a review station or another portable computing device for review. In some preferred embodiments, the examination data is converted from a form readable by the ultrasound system to a form readable by the portable computing device or review station. The ultrasound examination data can be transferred using a wired connection or using wireless technology, such an infrared communications link. The preferred embodiments can also be used with other medical acquisition devices and medical examination data. Examination data can also be transferred from medical networks, such as a medical diagnostic ultrasound imaging network.

The preferred embodiments will now be described with reference to the attached drawings.

DETAILED DESCRIPTION OF THE PRESENTLY PREFERRED EMBODIMENTS

Figure 1:
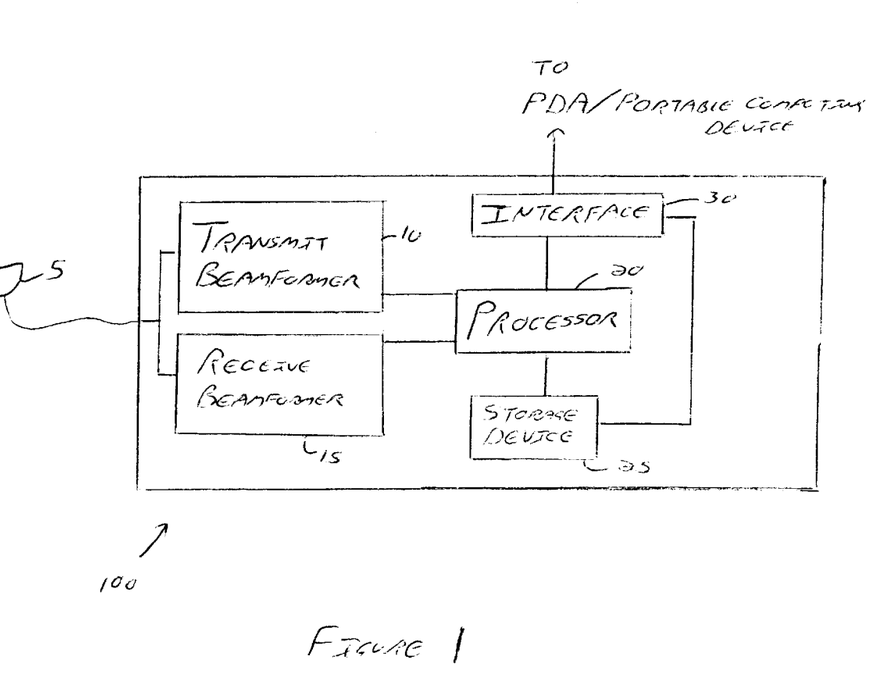
FIG. 1 is a block diagram of a medical diagnostic ultrasound imaging system of a presently preferred embodiment.

Turning now to the drawings, FIG. 1 is a block diagram of a medical diagnostic ultrasound imaging system 100 of a presently preferred embodiment. As shown in FIG. 1, the ultrasound system 100 comprises a transducer 5 coupled with a transmit beamformer 10 and a receive beamformer 15. As used herein, the term "coupled with" means directly coupled with or indirectly coupled with through one or more components. The beamformers 10, 15 are each coupled with a processor 20, which is coupled with a storage device 25. The term "processor" broadly refers to the appropriate hardware and/or software components of the ultrasound system 100 that can be used to implement the preferred embodiments described herein. It should be understood that any appropriate hardware (analog or digital) or software can be used and that the embodiments described herein can be implemented exclusively with hardware. Further, the processor 20 can be separate from or combined with (in whole or in part) other processors of the ultrasound system 100 (including attendant processors), which are not shown in FIG. 1 for simplicity. It should also be noted that the ultrasound imaging system 100 can comprise additional components. The ultrasound system 100 can be used with any suitable imaging mode (e.g., B-mode imaging, Doppler imaging, tissue harmonic imaging, contrast agent harmonic imaging, etc.), and the transducer 5 can be of any type (e.g., 1D, 1.5D, plano-concave, single element, phased-array, etc.).

In operation, the processor 20 causes the transmit beamformer 10 to apply a voltage to the transducer 5 to cause it to vibrate and emit an ultrasonic beam into an object, such as human tissue (i.e., a patient's body). Ultrasonic energy reflected from the body impinges on the transducer 5, and the resulting voltages created by the transducer 5 are received by the receive beamformer 15. The processor 20 processes the sensed voltages to create an ultrasound image associated with the reflected signals and displays the image on a display device (not shown). The processor 20 can also store the generated image and other ultrasound examination data in the storage device 25 (e.g., a hard drive). As used herein, the term "ultrasound examination data" is meant to broadly refer to ultrasound image data (still images and/or dynamic clips) and/or non-image data (such as calculation data and patient data) associated with an ultrasound examination.

In this preferred embodiment, the ultrasound system 100 also comprises a portable computing device interface 30, and, in operation, the processor 20 is operative to transfer ultrasound examination data from the storage device 25 to a portable computing device via the portable computing device interface 30. The portable computing device interface 30 can take any suitable form, such as, for example, a wireless communication device or a cradle that allows physical and electrical coupling between a portable computing device and the ultrasound system 100. For simplicity, the term "portable computing device" is used herein to broadly refer to any device comprising a processor and storage media that can be used to implement the embodiments described herein. While it is preferred that the portable computing device be a commercially-available, off-the-shelf product, the portable computing device can take the form of a customized device, such as one containing an application-specific processor, a wireless interface, a set of control buttons, and a storage unit (e.g., a Digital 8 microcassette).

Two examples of a portable computing device are a laptop computer (also known as a notebook computer) and a personal digital assistant (also known as a handheld or palmtop computer). A laptop computer is a full-fledged computer system that has a processor that typically includes an arithmetic and logical unit ("ALU"), a communications bus, connection-based network communications, rotating magnetic storage (such as a hard disk or floppy drive), and a video controller chip. A typical laptop is battery operated, weighs less than about five pounds, and has a thickness of less than about three-inches, allowing it to be transported and used in airplanes, libraries, temporary offices, and meetings. Laptop computers generally have the same capabilities as desktop computers and can be effectively turned into a desktop computer with a docking station.

In contrast to a typical laptop computer, a typical personal digital assistant (or "PDA") uses a digital signal processor ("DSP") instead of a central processor. Although a PDA contains a data storage device, it typically lacks rotating magnetic storage media. A PDA also lacks an ALU and a video controller, absorbing their functionality into the less-powerful DSP. Unlike laptop computers, PDAs run scaled-down versions of operating systems. For example, instead of using Microsoft's Windows 95/98, some PDAs use Microsoft's Windows CE, which is a small, scalable program that has a similar look-and-feel to Windows 95/98. Also unlike laptop computers which allow the same or virtually the same functionality as a desktop computer, a PDA is typically used merely to organize personal information (e.g., storing names, addresses, and phone numbers and maintaining schedules), enter notes, and perform simple calculations. Other PDAs offer pocket-sized versions of word processing and spreadsheet applications. Additionally, while some PDAs (such as the Jornada 820 Handheld PC from Hewlett-Packard) look like a laptop computer and use a touch-typeable keyboard, other PDAs (such as Palm Inc.'s PalmPilot) are small enough to be stored in a user's pocket and use a stylus, an electronically-sensitive pad, and handwriting recognition software (e.g., Grafitti).

Many PDAs use wireless technology (e.g., an infrared communications link) to transfer data to/from other computer systems and can also include telephony components to exchange e-mail and faxes, provide paging functions, and retrieve information from the Internet. PDAs can also transfer or receive data from another computer system via a wired connection. For example, a PDA can be physically and electrically coupled with a computer via a cradle. In operation, when a user slides the PDA into the cradle, electrical contacts on the PDA physically connect with electrical contracts on the cradle, allowing data transfer or synchronization between the computer and the PDA. Instead of a cradle, a cable can be used to physically and electrically connect the two devices.

Figures 2, 6:
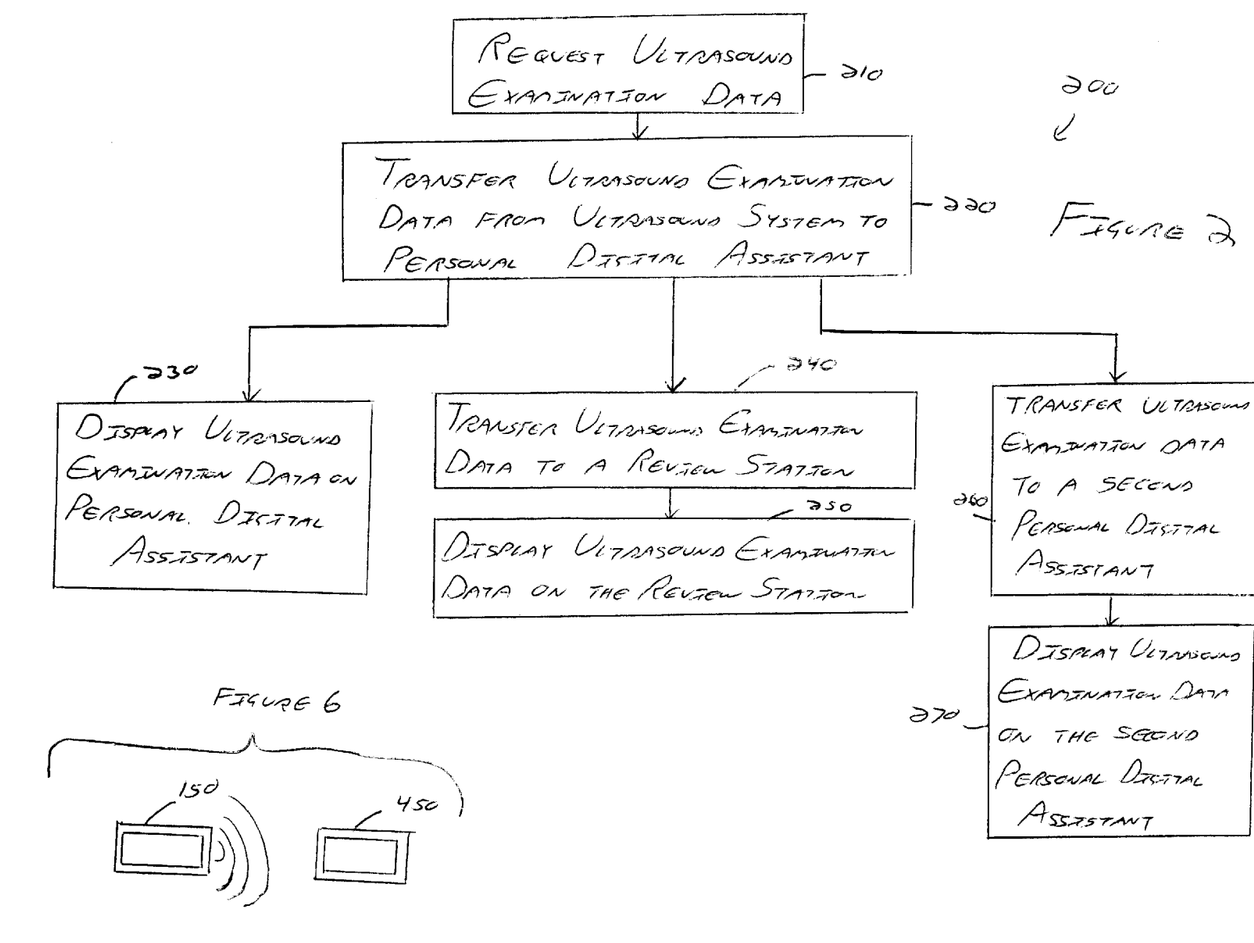
FIG. 2 is a flow chart of a method of a preferred embodiment for transferring ultrasound examination data from a medical diagnostic ultrasound imaging system to a portable computing device.
FIG. 6 is an illustration of a first portable computing device wirelessly communicating with a second portable computing device of a preferred embodiment.
Figure 3:
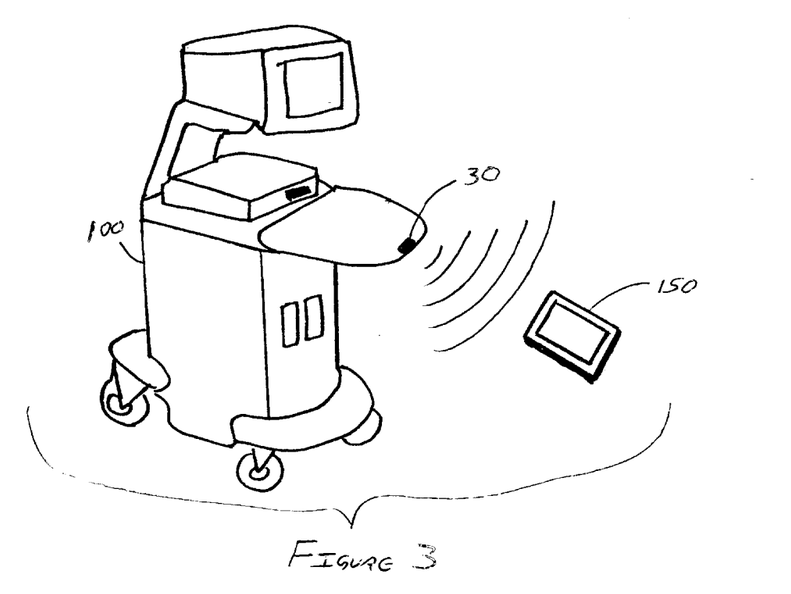
FIG. 3 is an illustration of a medical diagnostic ultrasound imaging system wirelessly communicating with a portable computing device of a preferred embodiment.

Turning again to the drawings, the ultrasound system 100 of FIG. 1 can be used in a method for transferring ultrasound examination data to a portable computing device. This preferred method will be illustrated in view of FIGS. 2 and 3. For simplicity, the preferred embodiments will be described in terms of a personal digital assistant, and the personal digital assistant interface 30 will be a wireless communication device that communicates with a wireless communication device of the personal digital assistant 150 using infrared technology. With reference to FIG. 3, a user brings the personal digital assistant 150 in the vicinity of the ultrasound system 100 and requests the transfer of ultrasound examination data from the ultrasound system 100 to the personal digital assistant 150 (act 210). In one preferred embodiment, the user issues this request by interacting with a user interface of the personal digital assistant 150. In response to this interaction, the processor of the personal digital assistant 150 issues a download command to the ultrasound system 100 via the wireless communication device of the personal digital assistant 150. In an alternate embodiment, the request is entered on the ultrasound system instead of on the personal digital assistant 150.

In response to the received download command, the processor 20 of the ultrasound system 100 wirelessly transfers ultrasound examination data stored in the storage device 25 to the personal digital assistant via the system's wireless communication device 30 (act 220). As discussed in more detail below, the processor 20 can also prepare the ultrasound examination data for transfer by changing the format of the data. While the ultrasound examination data is being wirelessly transferred, the ultrasound system 100 and/or the personal digital assistant 150 can display an activity indicator to assure the user that the transfer is in progress and to inform the user not to break the wireless link between the ultrasound system 100 and the personal digital assistant 150. When the download is complete, the ultrasound system 100 and/or the personal digital assistant 150 can display completion messages to the user, which, if preferred, can remain displayed until the user acknowledges the message. Upon completion of the transfer, the ultrasound system 100 returns to its previous state and is ready to perform another ultrasound examination.

Figure 4:
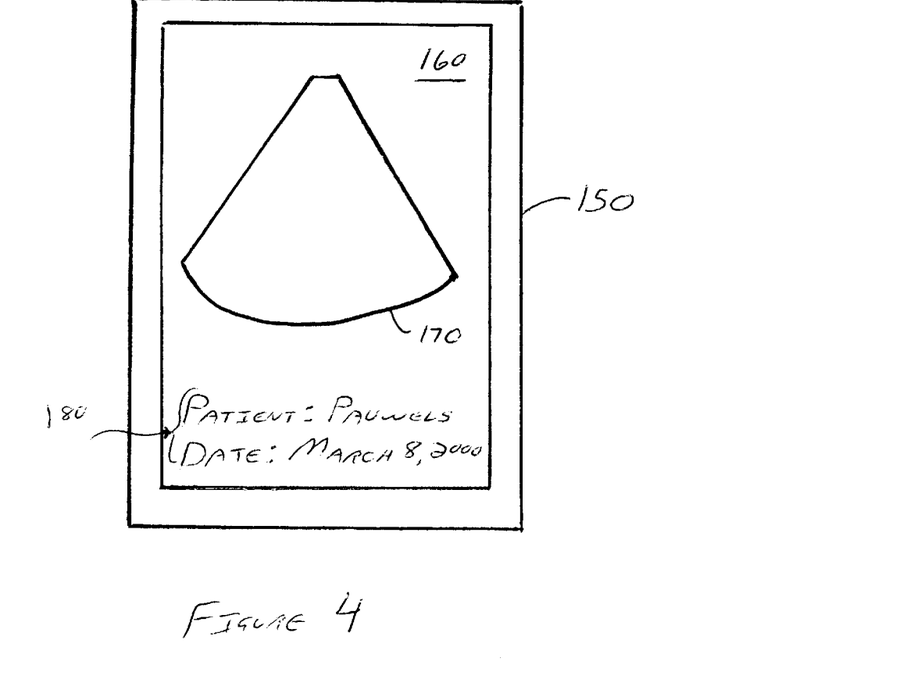
FIG. 4 is an illustration of a portable computing device of a preferred embodiment displaying ultrasound examination data transferred from a medical diagnostic ultrasound imaging system.

The downloaded ultrasound examination data is stored in a storage device of the personal digital assistant 150. If the ultrasound examination data is in the proper format, it can be viewed on a display device of the personal digital assistant 150 (act 230). Depending on the application, the personal digital assistant can use standard, off-the-shelf software or custom software to view the data. In the illustration shown in FIG. 4, the personal digital assistant 150 is displaying an ultrasound image 170 and patient data 180 of the transferred ultrasound examination data on its display device 160. The display continues until the user selects another function or powers-off the device.

There are several advantages associated with this preferred embodiment. First, because personal digital assistants are small enough to be carried in a jacket or shirt pocket, they can be carried by users almost at all times. This allows a physician to have ultrasound examination data handy whenever and wherever he wants to review the data. This also allows the physician to carry the ultrasound examination data to another venue for consulting or teaching purposes. Further, if the personal digital assistant belongs to a patient, he can carry the personal digital assistant home and review his examination data privately or with his family.

In another preferred embodiment, the personal digital assistant 150 is used as a "data runner" between the ultrasound system 100 and an ultrasound examination data review station. As used herein, the term "review station" is meant to broadly refer to any device to which examination data can be transferred for viewing purposes. A review station is typically a personal computer or workstation, such as the review station 300 shown in FIG. 5. Review stations often comprise one or more display device 310, 315, user interface elements (e.g., keyboard 320 and mouse 330), and a processor 340 operative to display, review, and analyze stored or retrieved examination data. The review station 300 can also run additional software applications. It is important to note that a review station can take other forms. For example, a review station can comprise a television with an attached set-top box or its own advanced networking functionality.

Figure 5:
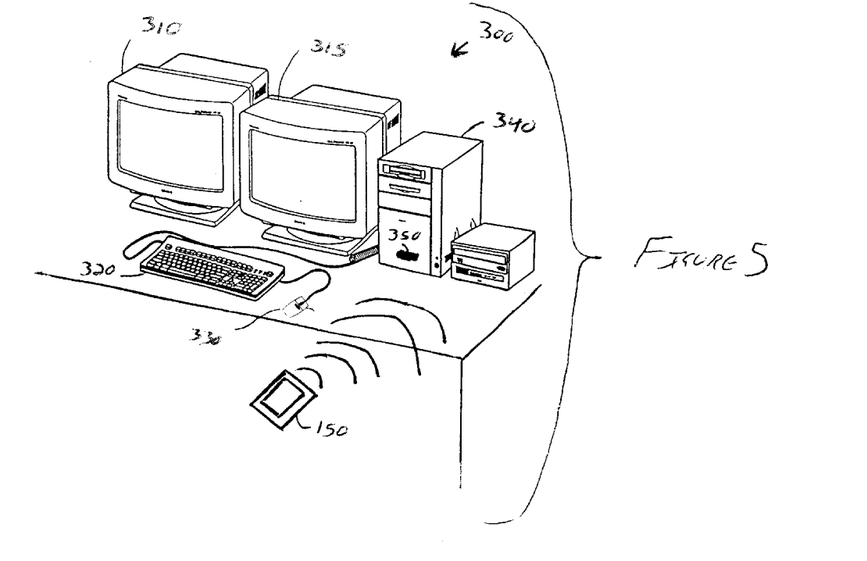
FIG. 5 is an illustration of a portable computing device of a preferred embodiment wirelessly communicating with an ultrasound examination data review station.

Turning again to the flow chart of FIG. 2, when the user brings the personal digital assistant 150 in the vicinity of review station 300, the user can employ the interface of the personal digital assistant 150 and/or the review station 300 to begin the upload process. For example, the user, exercising the user interface of the personal digital assistant 150, can issue an upload command to the review station 300 via a wireless link, such as an infrared link. The personal digital assistant 150 then wirelessly transmits the ultrasound examination data to the review station 300, which receives the data via a wireless receiver 350 (act 240). The personal digital assistant 150 and/or the review station 300 can display activity indicators while data transfer is taking place and can display completion messages at the conclusion of the upload process. The review station 300 can then display the transferred ultrasound examination data on its display device 310, 315 (act 250). If the review station 300 is programmed with an image review application, it can display two or more exams side-by-side either to compare the conditions of different patients or to demonstrate one patient's progress under treatment. This feature can also be useful in teaching or consulting settings. The ultrasound examination data can also be incorporated into a report being prepared by another software package. If the review station 300 is a patient's home computer, the patient can use his computer to privately review his images or show his images to his family. It should be noted that these are just some of the many applications that can be used in conjunction with the transferred ultrasound examination data.

There are several advantages associated with using a personal digital assistant to transfer ultrasound examination data from an ultrasound system to a review station. First, unlike the sneakernet approach using videotapes or diskettes, the use of a personal digital assistant does not require the user to know how to operate the ultrasound system—the user merely needs to know how to operate the easy-to-use user interface of the personal digital assistant. Additionally, because many people are already using personal digital assistants for other purposes (e.g., personal information management), using a personal digital assistant to transfer examination data is an efficient use of resources and does not require additional hardware. Further, because personal digital assistants are digital and durable, they are not susceptible to many of the problems that are associated with videotape and allow transfer of examination data to computers and televisions that do not have a VCR connected to them. Finally, when stored in a computer environment, the examination data can be archived and preserved more effectively because it is kept in a standard image format.

In yet another preferred embodiment, the personal digital assistant 150 is used to transfer ultrasound examination data to a second personal digital assistant. With reference to FIGS. 2 and 6, the user brings the first personal digital assistant 150 in the vicinity of a second personal digital assistant 450. Using control software on the first or second personal digital assistants 150, 450, the user begins the upload/download process to transfer ultrasound examination data stored in the first personal digital assistant 150 to the second personal digital assistant 450 (act 260). The transferred data is stored in the second personal digital assistant 450 and can be viewed on its display device (act 270). This allows multiple users to easily exchange ultrasound examination data through wireless transfer from one personal digital assistant to another. This feature finds particular utility in hospitals and other environments where many users in a community have personal digital assistants.

Figure 7:
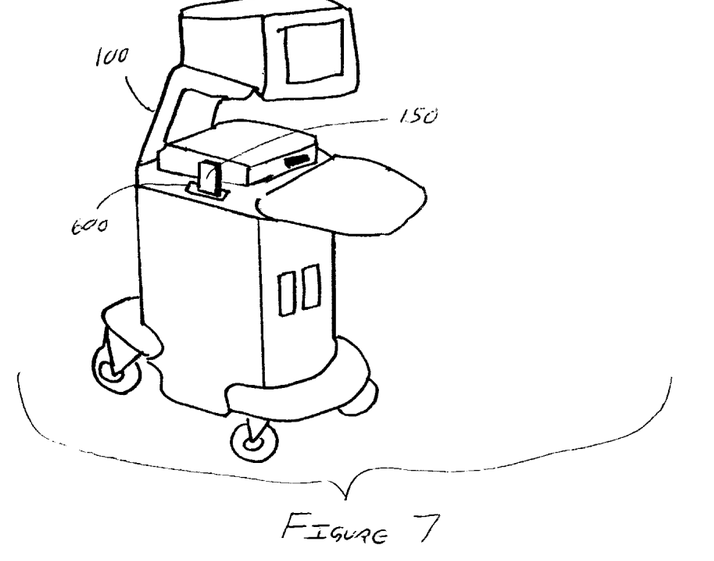
FIG. 7 is an illustration of a medical diagnostic ultrasound imaging system of a preferred embodiment coupled with a portable computing device via a portable communication device interface.
Figure 8:
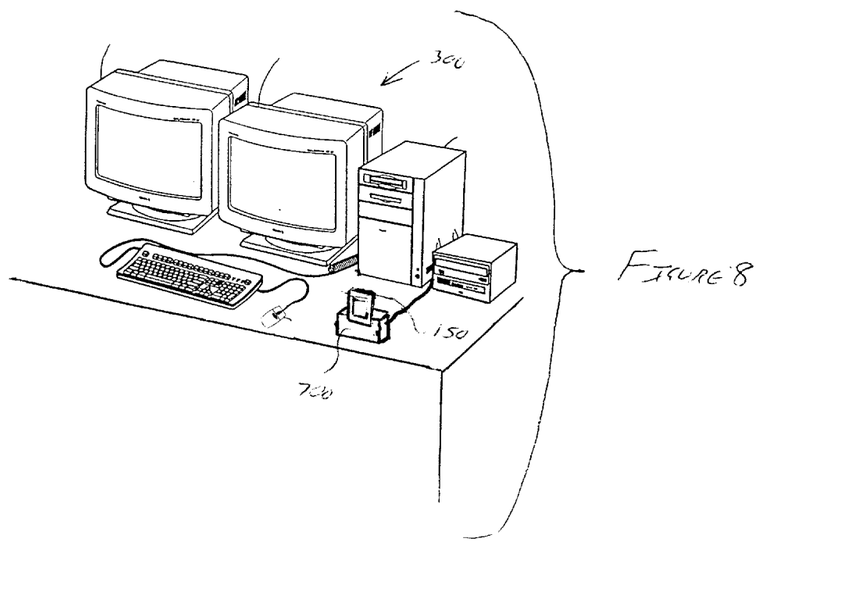
FIG. 8 is an illustration of an ultrasound examination data review station of a preferred embodiment coupled with a portable computing device via a portable communication device interface.

There are several alternatives that can be employed with these preferred embodiments. For example, in the preferred embodiments described above, the personal digital assistant 150 communicated with the ultrasound system 100 and the review station 300 via a wireless communication link. In one alternate embodiment, instead of or in addition to using a wireless communication link, the personal digital assistant 150 receives and/or transfers ultrasound examination data through a wired connection. As shown in the illustrations of FIGS. 7 and 8, the personal digital assistant 150 can be coupled with a cradle 600, 700 of the ultrasound system 100 and/or the review station 300. In operation, electrical contacts on the personal digital assistant 150 couple with electronic contacts on the cradle 600, 700, allowing ultrasound examination data to be transferred from one device to the other. This alternate embodiment finds particular utility in situations where a user already had a personal-digital-assistant cradle attached to his computer to synchronize data stored in his personal digital assistant with data stored in his computer. In this situation, the user can transfer ultrasound examination data to his computer without purchasing any additional hardware. In another alternate embodiment, instead of a cradle, the wired connection takes the form of a physical wire or cable that attaches at one end to the ultrasound system (or review station) and attaches at the other end to the personal digital assistant.

As noted above, the processor 20 can prepare the ultrasound examination data for transfer by changing the format of the data. In many applications, ultrasound examination data is stored in the ultrasound system using a format that is proprietary to the manufacturer of the ultrasound system. In these applications, the ultrasound system can convert the format of the data from a form readable by the ultrasound system to a form readable by the personal digital assistant or the review station, such as JPG or another suitable industry standard format. This conversion process may involve separating the colors into hue, chrominance, and saturation components and individually compressing each of these components; attaching examination information (e.g., patient name and ID, date, type of study); attaching calibration information; and attaching header data to support the DICOM standard. Although the image formatting can occur at the personal digital assistant, it is preferred that the image formatting occur at the ultrasound system since an ultrasound system typically has greater computing power than a personal digital assistant. The image formatting can also occur at the review station. Examination data formatting can also include compressing the data to reduce the time needed to transfer the image.

Because many personal digital assistants have a more limited display capability (e.g., limited screen size and resolution) as compared to ultrasound systems or review stations, additional formatting may be required to view the data on the personal digital assistant. For example, some personal digital assistants, such as the Palm Pilot, use as a native file format called PRC, which is adapted from the resource fork in older versions of MacOS. PRC is a combined format that can describe either Palm executables or visual images, and a PRC file begins with a common header block that expresses the kind and quantity of information in the file and the means by which the personal digital assistant should interpret the contents. A software program for the Palm Pilot called "Image Extractor" displays images in the PRC format and also displays images in a bitmap ("BMP") format. BMP is an old and well-known image format, and there are several free programs (such as xv and PBM) in the Linux domain that translate from JPG to BMP. Accordingly, in one preferred embodiment, after the image data is converted to a JPG format, it is converted to a BMP image and then transferred to the personal digital assistant for viewing. In another preferred embodiment, only the scale and resolution of the ultrasound image is reduced from a full-size image format to an "icon." "thumbnail," or "postage stamp" format.

In the preferred embodiments discussed above, examination data was wirelessly transferred using a wireless communication link and a wireless communication device. For simplicity, the term "wireless" has been used to broadly refer to any technology that allows the transfer of examination data from one point to another without the use of a physical connection. Because infrared technology is widely-used with PDAs and other portable computing devices, it is preferred that the wireless communication device employ infrared technology. However, other wireless technologies, such as but not limited to radio frequency, light wave, or microwave transmissions, can be used. It should also be noted that the wireless communication device can be an integral/built-in component or an add-on component (such as a detachable accessory) and that the wireless communication device can include an emitter, receiver, and/or transceiver. Further, data can be wirelessly transmitted in analog or digital form. The following two patent applications assigned to the assignee of the present invention relate to wireless transmissions and are hereby incorporated by reference: "Diagnostic Medical Ultrasound System with Wireless Communication Device" (U.S. application Ser. No. 09/237,548; filed Jan. 26, 1999, now U.S. Pat. No. 6,241,673) and "Medical Diagnostic Ultrasound Imaging System with a Wirelessly-Controlled Peripheral" (U.S. application Ser. No. 09/538,449; filed on the same day as the present patent application now U.S. Pat. No. 6,238,344).

Lastly, while the preferred embodiments were described above in terms of medical diagnostic ultrasound imaging system and ultrasound examination data, it should be understood that these preferred embodiments can be applied to any suitable medical diagnostic image acquisition device and medical examination data generated therefrom. For example, a medical diagnostic image acquisition device that employs any of the following modalities can be used: computed radiography, magnetic resonance, angioscopy, color flow Doppler, cystoscopy, diaphanography, echocardiography, fluoresosin angiography, laparoscopy, magnetic resonance angiography, positron emission tomography, single-photon emission computed tomography, x-ray angiography, computed tomography, nuclear medicine, biomagnetic imaging, culposcopy, duplex Doppler, digital microscopy, endoscopy, fundoscopy, laser surface scan, magnetic resonance spectroscopy, radiographic imaging, thermography, and radio fluroscopy. Further, examination data can also be transferred from medical networks, such as a medical diagnostic ultrasound imaging network, a hospital information system, or a picture archive and communication system. As with ultrasound examination data, medical examination data can comprise image and/or non-image data.

It is important to note that any of the various aspects of any of the preferred embodiments can be used alone or in combination. For example, the portable computing device that is used to transfer examination data from an ultrasound system to a review station may or may not also have the functionality to view the image. Also, as stated above, although the preferred embodiments were described in conjunction with a personal digital assistant, any type of portable computing device (such as a laptop computer) can be used.

It is intended that the foregoing detailed description be understood as an illustration of selected forms that the invention can take and not as a definition of the invention. It is only the following claims, including all equivalents, that are intended to define the scope of this invention.

What is claimed is:

1. A medical diagnostic ultrasound imaging system comprising;
   a transmit beamformer;
   a receive beamformer;
   a transducer coupled with the transmit and receive beamformers;
   a processor coupled with the transmit and receive beamformers and operative to generate an ultrasound image from an output of the receive beamformer;
   a storage device storing an ultrasound image generated by the processor; and
   a personal digital assistant interface;
   wherein the processor is operative to transfer the ultrasound image stored in the storage device to a personal digital assistant via the personal digital assistant interface.

2. The invention of claim 1, wherein the processor is further operative to convert the ultrasound image to a form readable by the personal digital assistant.

3. The invention of claim 1, wherein the personal digital assistant interface comprises a wireless communication device, and wherein the processor is further operative to wirelessly transfer the ultrasound image stored in the storage device to the personal digital assistant via the wireless communication device.

4. The invention of claim 1, wherein the personal digital assistant interface comprises a personal-digital-assistant cradle, and wherein the processor is further operative to wirelessly transfer the ultrasound image stored in the storage device to the personal digital assistant via the personal-digital-assistant cradle.

5. The invention of claim 1, wherein the ultrasound image comprises a dynamic clip.

6. The invention of claim 1, wherein the ultrasound image comprises a still image.

7. The invention of claim 1, wherein the storage device further stores calculation data associated with the ultrasound image, and wherein the processor is further operative to transfer the calculation data stored in the storage device to a personal digital assistant via the personal digital assistant interface.

8. The invention of claim 1, wherein the storage device further stores patient data associated with the ultrasound image, and wherein the processor is further operative to transfer the patient data stored in the storage device to a personal digital assistant via the personal digital assistant interface.

9. For use with a medical diagnostic ultrasound imaging system comprising a transmit beamformer, a receive beamformer, and a transducer coupled with the transmit and receive beamformers, a method for transferring an ultrasound image from the medical diagnostic ultrasound imaging system to a personal digital assistant, the method comprising:

(a) transferring an ultrasound image from a medical diagnostic ultrasound imaging system to a personal digital assistant via a personal digital assistant interface of the medical diagnostic ultrasound imaging system;

(b) storing the ultrasound image in the personal digital assistant; and (c) displaying the ultrasound image on a display of the personal digital assistant.

10. The invention of claim 9, wherein the personal digital assistant interface comprises a wireless communication device, and wherein (a) comprises wirelessly transferring the ultrasound image from the medical diagnostic ultrasound imaging system to the personal digital assistant via the wireless communication device.

11. The invention of claim 9, wherein the personal digital assistant interface and the personal digital assistant each comprises at least one electrical contact, and wherein (a) further comprises the act of physically and electrically coupling the at least one electrical contact of the personal digital assistant with the at least one electrical contact of the personal digital assistant interface.

12. The invention of claim 11, wherein the personal digital assistant interface comprises a personal digital assistant cradle.

13. The invention of claim 9 further comprising converting the ultrasound image to a form readable by the personal digital assistant.

14. The invention of claim 9 further comprising receiving a request from the personal digital assistant for the ultrasound image, said act of receiving occurring before act (a).

15. The invention of claim 9 further comprising:

(d) transferring the ultrasound image from the personal digital assistant to an ultrasound image review station.

16. The invention of claim 9 further comprising:

(d) transferring the ultrasound image from the personal digital assistant to a second personal digital assistant.

17. The invention of claim 9 further comprising:

(d) transferring calculation data associated with the ultrasound image from the medical diagnostic ultrasound imaging system to the personal digital assistant via the personal digital assistant interface of the medical diagnostic ultrasound imaging system;

(e) storing the calculation data in the personal digital assistant; and (f) displaying the calculation data on the display of the personal digital assistant.

18. The invention of claim 9 further comprising:

(d) transferring patient data associated with the ultrasound image from the medical diagnostic ultrasound imaging system to the personal digital assistant via the personal digital assistant interface of the medical diagnostic ultrasound imaging system;

(e) storing the patient data in the personal digital assistant; and (f) displaying the patient data on the display of the personal digital assistant.

19. For use with a medical diagnostic ultrasound imaging system comprising a transmit beamformer, a receive beamformer, and a transducer coupled with the transmit and receive beamformers, a method for transferring an ultrasound image from the medical diagnostic ultrasound imaging system to an ultrasound image review station, the method comprising:

(a) transferring an ultrasound image from a medical diagnostic ultrasound imaging system to a portable computing device via a portable computing device interface of the medical diagnostic ultrasound imaging system;

(b) storing the ultrasound image in the portable computing device; and (c) transferring the ultrasound image from the portable computing device to an ultrasound image review station.

20. The invention of claim 19, wherein the portable computing device interface comprises a wireless communication device, and wherein (a) comprises wirelessly transferring the ultrasound image from the medical diagnostic ultrasound imaging system to the portable computing device via the wireless communication device.

21. The invention of claim 19, wherein the portable computing device and the portable computing device interface each comprises at least one electrical contact, and wherein (a) further comprises the act of physically and electrically coupling the at least one electrical contact of the portable computing device with the at least one electrical contact of the portable computing device interface.

22. The invention of claim 19, wherein (c) comprises wirelessly transferring the ultrasound image from the portable computing device to the ultrasound image review station.

23. The invention of claim 19, wherein the portable computing device and the ultrasound image review station each comprises at least one electrical contact, and wherein (c) further comprises the act of physically and electrically coupling the at least one electrical contact of the portable computing device with the at least one electrical contact of the ultrasound image review station.

24. The invention of claim 19 further comprising converting the ultrasound image to a form readable by the ultrasound image review station.

25. The invention of claim 19 wherein the portable computing device comprises a personal digital assistant.

26. The invention of claim 19 wherein the portable computing device comprises a laptop computer.

27. The invention of claim 19 further comprising:

(d) transferring calculation data associated with the ultrasound image from the medical diagnostic ultrasound imaging system to the portable computing device via the portable computing device interface of the medical diagnostic ultrasound imaging system;

(e) storing the calculation data in the portable computing device; and (f) transferring the calculation data from the portable computing device to the ultrasound image review station.

28. The invention of claim 19 further comprising:

(d) transferring patient data associated with the ultrasound image from the medical diagnostic ultrasound imaging system to the portable computing device via the portable computing device interface of the medical diagnostic ultrasound imaging system;

(e) storing the patient data in the portable computing device; and (f) transferring the patient data from the portable computing device to the ultrasound image review station.

29. For use with a medical diagnostic ultrasound imaging system comprising a transmit beamformer, a receive beamformer, and a transducer coupled with the transmit and receive beamformers, a method for wirelessly transferring an ultrasound image from the medical diagnostic ultrasound imaging system to a portable computing device, the method comprising:

(a) wirelessly transferring an ultrasound image from a medical diagnostic ultrasound imaging system to a portable computing device via a wireless communication device of the medical diagnostic ultrasound imaging system;

(b) storing the ultrasound image in the portable computing device; and (c) displaying the ultrasound image on a display of the portable computing device.

30. The invention of claim 29 further comprising:

(d) wirelessly transferring calculation data associated with the ultrasound image from the medical diagnostic ultrasound imaging system to the portable computing device via the wireless communication device of the medical diagnostic ultrasound imaging system;

(e) storing the calculation data in the portable computing device; and (f) displaying the calculation data on the display of the portable computing device.

31. The invention of claim 29 further comprising:

(d) wirelessly transferring patient data associated with the ultrasound image from the medical diagnostic ultrasound imaging system to the portable computing device via the wireless communication device of the medical diagnostic ultrasound imaging system;

(e) storing the patient data in the portable computing device; and (f) displaying the patient data on the display of the portable computing device.

32. A method for transferring a medical image from a medical diagnostic image acquisition device to a personal digital assistant, the method comprising:

(a) transferring a medical image from a medical diagnostic image acquisition device to a personal digital assistant via a personal digital assistant interface of the medical diagnostic image acquisition device;

(b) storing the medical image in the personal digital assistant; and (c) displaying the medical image on a display of the personal digital assistant.

33. A method for transferring a medical image from a medical diagnostic image acquisition device to a medical image review station, the method comprising:

(a) transferring a medical image from a medical diagnostic image acquisition device to a portable computing device via a portable computing device interface of the medical diagnostic image acquisition device;

(b) storing the medical image in the portable computing device; and (c) transferring the medical image from the portable computing device to a medical image review station.

34. A method for wirelessly transferring a medical image from a medical diagnostic image acquisition device to a portable computing device, the method comprising:

(a) wirelessly transferring a medical image from a medical diagnostic image acquisition device to a portable computing device via a wireless communication device of the medical diagnostic image acquisition device;

(b) storing the medical image in the portable computing device; and (c) displaying the medical image on a display of the portable computing device.

35. A method for wirelessly transferring a medical image from a medical image network to a portable computing device, the method comprising:

(a) wirelessly transferring a medical image from a medical image network to a portable computing device;

(b) storing the medical image in the portable computing device, and (c) performing at least one of:
   (c1) displaying the medical image on a display of the portable computing device;
   (c2) transferring the medical image from the portable computing device to a medical image review station.

* * * * *